(12) United States Patent
Pounds et al.

(10) Patent No.: US 10,632,261 B2
(45) Date of Patent: Apr. 28, 2020

(54) SELF-ADMIXING DISPOSABLE HYPODERMIC NEEDLE

(71) Applicant: Aurim, LLC, Colorado Springs, CO (US)

(72) Inventors: William E Pounds, Colorado Springs, CO (US); Jason Streeter, Colorado Springs, CO (US)

(73) Assignee: Aurim, LLC, Colorado Springs, CO (US)

( * ) Notice: Subject to any disclaimer, the term of this patent is extended or adjusted under 35 U.S.C. 154(b) by 0 days.

(21) Appl. No.: 16/546,917

(22) Filed: Aug. 21, 2019

(65) Prior Publication Data

US 2020/0061294 A1   Feb. 27, 2020

Related U.S. Application Data

(60) Provisional application No. 62/721,470, filed on Aug. 22, 2018.

(51) Int. Cl.
*A61M 5/24* (2006.01)
*A61M 5/178* (2006.01)
(Continued)

(52) U.S. Cl.
CPC ........ *A61M 5/2448* (2013.01); *A61M 5/1782* (2013.01); *A61M 5/284* (2013.01);
(Continued)

(58) Field of Classification Search
CPC ...... A61M 5/1782; A61M 5/28; A61M 5/284; A61M 5/283; A61M 5/288; A61M 5/3297;
(Continued)

(56) References Cited

U.S. PATENT DOCUMENTS 3,161,195 A   12/1964   Taylor et al.
4,031,892 A   6/1977   Hurschman
(Continued)

FOREIGN PATENT DOCUMENTS

WO   WO2007101772 A1   9/2007

OTHER PUBLICATIONS

PCT International Search Report, PCT/US2019/047472, dated Oct. 16, 2019.

*Primary Examiner* — Kevin C Sirmons
*Assistant Examiner* — Alexandra Lalonde
(74) *Attorney, Agent, or Firm* — Mehrman Law Office; Michael J. Mehman

(57) ABSTRACT

A self-admixing disposable hypodermic needle (admixing needle) includes a reservoir containing an additive, such as a buffering agent, to facilitate homogeneous mixing of the additive with an injection fluid, such as Lidocaine, contained in a cartridge held within a mechanically conjoined syringe. The admixing needle establishes a fluid communication pathway for hypodermically delivering the injection mixture to a patient preceding a potentially painful dental or medical procedure. Prior to removal, a delivery needle cap is pushed toward the syringe to dispense the additive into the cartridge. The delivery needle is then placed within the patient's tissues and the syringe is operated to force the injection mixture from the cartridge. Mixing surfaces on the male body (reservoir plunger) and the female body (reservoir) and other mechanical features homogeneously combine the injection fluid with the additive as the injection mixture travels through the admixing needle during the hypodermic injection.

9 Claims, 8 Drawing Sheets

(51) Int. Cl.
*A61M 5/28* (2006.01)
*A61M 5/32* (2006.01)
*A61M 5/31* (2006.01)
*A61J 1/20* (2006.01)
*A61M 5/19* (2006.01)

(52) U.S. Cl.
CPC .......... *A61M 5/3202* (2013.01); *A61J 1/2006* (2015.05); *A61M 5/19* (2013.01); *A61M 5/3234* (2013.01); *A61M 2005/3109* (2013.01)

(58) Field of Classification Search
CPC .............. A61M 5/2422; A61M 5/2448; A61M 5/2066; A61M 5/31596; A61M 5/19; A61M 5/3294; A61M 5/3202; A61M 5/2466; A61M 5/329; A61M 5/3293; A61M 5/2429; A61M 5/348; A61M 2005/31598; A61M 2005/2451; A61M 2005/1787; A61M 2005/247; A61M 2005/2474; A61M 2005/2407; A61M 2005/2411; A61M 2005/2488; A61M 2005/3139; A61M 2039/042; A61M 5/285; A61M 5/286; A61M 5/2455; A61M 5/2459; A61M 5/2425; A61M 2005/2462; A61M 2005/287; B05B 11/0078; B05B 11/02; A61J 1/2031; A61J 1/2003; A61J 1/2017; A61J 1/2006; A61J 1/201; A61J 1/20; A61J 1/202; A61J 1/2048; A61J 1/2051; A61J 1/2089; A61J 1/2096; A61J 1/2013; A61J 1/2093; A61J 1/2065; A61J 1/2062; A61J 1/22; A61J 1/2079; A61J 1/1487; A61J 1/2027; A61J 1/2037; A61J 1/2041; A61J 1/2044; B65D 81/32; B65D 25/08; B65D 25/085; B65D 51/18

See application file for complete search history.

(56) References Cited

U.S. PATENT DOCUMENTS

| | | |
|---|---|---|
| 4,154,820 A | 5/1979 | Simmons |
| 4,592,745 A | 6/1986 | rex et al. |
| 5,281,198 A | 1/1994 | Haber et al. |
| 5,360,410 A | 11/1994 | Wacks |
| 5,445,614 A | 8/1995 | Haber et al. |
| 5,603,695 A | 2/1997 | Erickson |
| 6,224,568 B1* | 5/2001 | Morimoto ............. A61J 1/2089 604/89 |
| 7,329,235 B2 | 2/2008 | Bertron et al. |
| 7,731,678 B2 | 6/2010 | Tennican et al. |
| 7,776,011 B2 | 8/2010 | Tennican et al. |
| 7,944,691 B1 | 5/2011 | Pounds |
| 8,430,843 B2 | 4/2013 | Chebator et al. |
| 8,690,853 B2 | 4/2014 | Stepovich et al. |
| 8,834,449 B2 | 9/2014 | Machan et al. |
| 8,900,513 B2 | 12/2014 | Christian et al. |
| 9,205,194 B2 | 12/2015 | Mojdehbakhsh et al. |
| 9,387,151 B2 | 7/2016 | Davidian et al. |
| 2005/0277895 A1* | 12/2005 | Giambattista ......... A61M 5/002 604/198 |
| 2011/0166543 A1* | 7/2011 | Stepovich ............. A61J 1/2096 604/413 |
| 2012/0172793 A1* | 7/2012 | Cronenberg .......... A61J 1/2096 604/87 |
| 2014/0163465 A1* | 6/2014 | Bartlett, II ........ A61M 5/31596 604/90 |
| 2014/0254303 A1 | 9/2014 | McArthur et al. |
| 2015/0053305 A1 | 2/2015 | Davidian et al. |

* cited by examiner

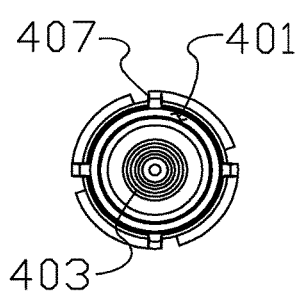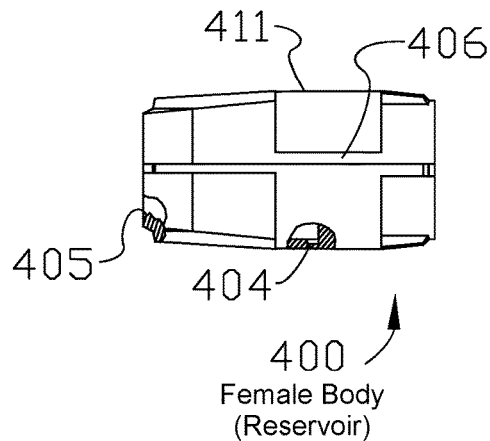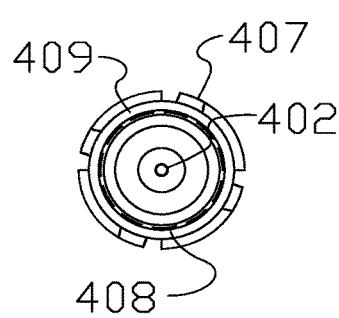
Fig. 4B
Fig. 4A
400
Female Body
(Reservoir)
Fig. 4C
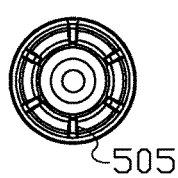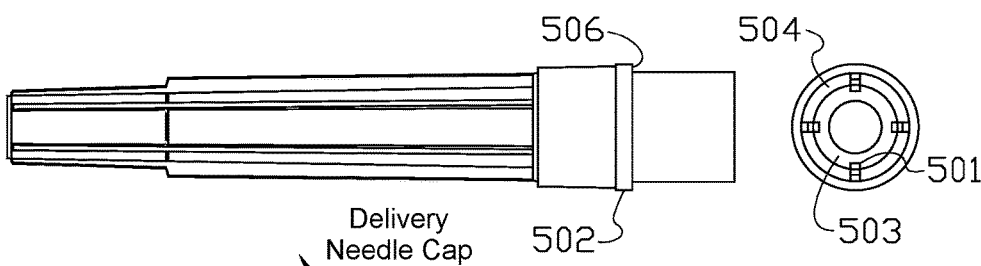
Fig. 5B
Fig. 5A
Delivery Needle Cap
500
Fig. 5C
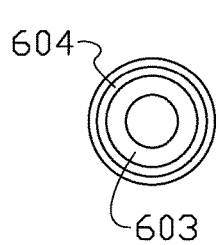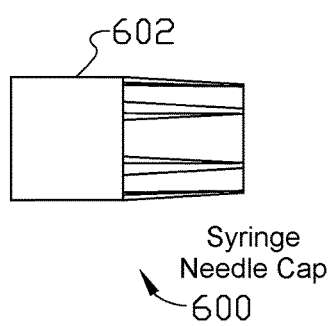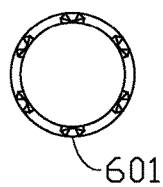
Fig. 6B
Fig. 6A
Syringe Needle Cap
600
Fig. 6C

SELF-ADMIXING DISPOSABLE HYPODERMIC NEEDLE

REFERENCE TO RELATED APPLICATION

This application claims priority to U.S. Provisional Patent Application Ser. No. 62/721,470 filed Aug. 22, 2018, which is incorporated by reference.

TECHNICAL FIELD

The present invention is directed to syringes and, more particularly, to a self-admixing disposable hypodermic needle and process for dental, medical, and other admixing purposes.

BACKGROUND

Certain dental or medical procedures cause unbearable discomfort to the patient and require some form of local anesthesia prior to commencement. The central nervous system is responsible for processing sensory information relayed by sensory neurons called receptor cells, neural pathways, and parts of the brain involved in sensory perception. Senses are transducers from the physical world to the mind, via the central nervous system, where we interpret the information, creating our perception of the world around us.

There are two basic types of anesthesia in use. The first is a general anesthesia which causes a full loss of consciousness thereby adding serious risk to the patient. The second is a temporarily induced and fully reversable local anesthesia which has significantly less risk to the patient facilitated by parenteral placement via hypodermic needle of a local anesthetic like Lidocaine® to suppress the pain sensing and signal transduction pathway to the brain via nerves near the procedure site alleviating the pain.

Local anesthetic solutions commonly have an acidic pH level of around 3.5 to extend their shelf life and enhance stability thus making them significantly different from the human body's normal pH level. A delay in the onset of anesthesia is caused by the time needed for the body to naturally neutralize the anesthetic preparation's low pH which is required to enable the anesthetic to pass through the walls of the sensory nerve cells.

By mixing the local anesthetic solution with a predetermined amount of a neutralizing solution like sodium bicarbonate having a pH of around 8.4 just prior administering it to the patient, the pH of the local anesthetic can be adjusted to be closer to the patient's body pH of 7.4 to facilitate a shorter onset time of anesthesia and more pronounced anesthetic effect which is beneficial to the patient. This also increases the efficiency of the dentist, or medical practitioner by reducing the time required to complete the painful procedure.

The process of modifying the pH of a final preparation is known to those skilled in the art as alkalization or buffering. If the preparation is buffered too far in advance of its use, it will precipitate and form solid crystals which could cause tissue damage or additional pain or discomfort if injected into a patient. Over time, the pH levels of preparations buffered too far in advance will also continue to rise.

Others have provided commercially available devices to buffer local anesthetic preparations. This includes the Onpharma® buffering pen. This system is complicated to use and subject to error as it has many steps that need to be performed in a specific sequence, each of which takes time. Due to the sheer number of injections administered each day by the dentist or medical practitioner, this device is cumbersome and impractical to use.

Another downfall of existing anesthetic buffering systems, especially Anutra® is that they take up precious counter space in the operatory as well as increasing inventory with costly disposables, special syringes, and handheld peripheral components requiring storage space in the dental office.

There is, therefore, a need for an improved device and process for buffering local anesthetics immediately prior to administration to the patient on demand.

SUMMARY

The invention may be embodied in a self-admixing disposable hypodermic needle (also referred to as an "admixing needle" for descriptive convenience) and a procedure for its use to hypodermically inject a combined injection mixture, such as buffered Lidocaine, into a patient for the purposes of local anesthesia. The admixing needle includes a reservoir containing a predetermined amount of an additive (e.g., a buffering agent) to be mixed with an injection fluid (e.g., Lidocaine) to create a combined injection mixture to be injected from a cartridge by a syringe, such as an aspirating syringe. The admixing needle is attached to the syringe, which holds the injection fluid cartridge, with the cartridge needle extending into the cartridge. A delivery needle cap is then pushed toward the syringe to push a reservoir plunger into the reservoir to force the additive out of the reservoir, through the cartridge needle, and into the cartridge. This dispenses the additive from the reservoir of the admixing needle into the cartridge to create an injection mixture within the cartridge. The thumb ring is then used to push the syringe plunger towards the admixing needle to force the injection mixture from the cartridge back through the admixing needle and into the patient. Mixing surfaces on the reservoir plunger and reservoir homogeneously combine the injection fluid from the cartridge with the additive from the admixing needle as they pass back through, and out of, the admixing needle and hypodermically into the patient.

BRIEF DESCRIPTION OF THE DRAWINGS

FIGS. 4A-4C include a side view with two sectional interior views and both orthogonal end views of a female body (reservoir) on the admixing needle.

FIGS. 5A-5C include a side view and both orthogonal end views of a delivery needle cap on the admixing needle.

FIGS. 6A-6C include a side view and both orthogonal end views of a cartridge needle cap on the admixing needle.

DETAILED DESCRIPTION OF REPRESENTATIVE EMBODIMENTS

Figure 1:
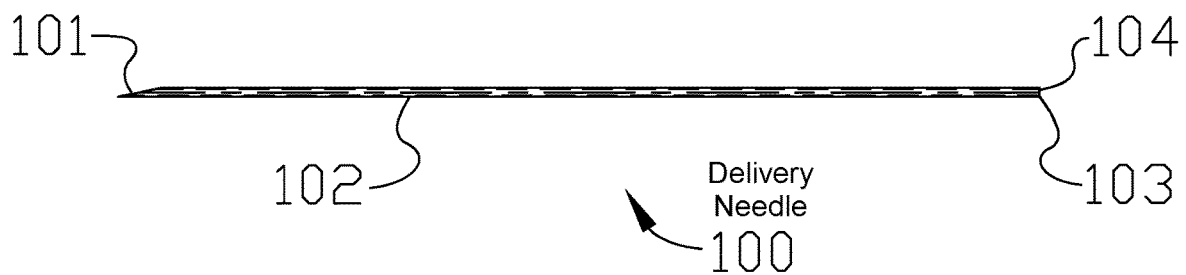
FIG. 1 is a side view of a delivery needle on a admixing needle.

The present invention may be embodied in a self-admixing disposable hypodermic needle (also referred to as an "admixing needle" for descriptive convenience) and related process for homogeneous admixing of two or more constituents into a final preparation on demand capable of combining two or more liquids or gasses or a liquid and a powder together upon their expulsion from the admixing needle to buffer or mix the final preparation just prior to administering, obviating the issues associated with pre-buffering or mixing too far in advance of the procedure or use. The admixing needle is operated in a manner that is very similar to the standard hypodermic needles commonly employed today with only a single additional step that takes less than one second to accomplish.

The onset time of the local anesthetic prevents the dentist or medical practitioner from performing procedures that would cause the patient pain until the local anesthesia effect is complete as the receptor nerves or signal pathways are still functioning normally and the patient would feel it. This causes a wide variety of delays from one patient to another. The buffered anesthetic solution facilitates higher lipid solubility allowing it to pass readily through the sensory nerve cell wall and makes the anesthetic more potent by increasing its effectiveness so that a lesser amount may be used to get a more profound and longer-lasting anesthesia effect.

The process of induced local anesthesia begins with the hypodermic placement of the local anesthetic parenterally in proximity of the nerve intended to be blocked near the proposed procedure site via a syringe, such as an aspirating syringe, through a admixing needle that intentionally inhibits the transmit or receive function of the local sensory nerves' signaling ability along metabolic pathways in response to pain or other noxious stimuli during normal cellular biochemical cascade eliminating the pain response to the patient which allows the painful procedure to be completed sooner because of the buffered preparation's reduced onset time or latency.

The admixing needle can be used to administer local anesthetics which are membrane-stabilizing pharmaceuticals that reversibly decrease the rate of depolarization of excitable membranes (like nociceptors) and prevent them from reacting to external stimuli. By inhibiting the sodium influx through sodium-specific ion channels in neuronal cell membranes, in particular, voltage-gated sodium channels which prevent the influx of sodium so that an action potential cannot arise, and signal conduction is inhibited. These receptors are located at the cytoplasmic (inner) portion of the sodium channel.

A local anesthetic like Lidocaine works by moving to the inside of a nerve cell and then binding to the sodium channel and in doing so blocks the influx of sodium ions which prevents nerve conduction thus prohibits further pain signals from reaching the brain.

Any dental or medical procedure involving the hypodermic injection of local anesthetic can be responsible for some amount of patient pain and anxiety. The main benefits of the admixing needle are the buffering of the local anesthetic preparation on demand (just prior to injection) to prevent the patient from experiencing pain sooner and more completely, which in turn reduces the patient's anxiety. The admixing needle also produces an increased and more pronounced anesthetic effect with longer lasting duration using less pharmaceutical to get the same benefit. Additionally, the $CO_2$ generated as a byproduct of the pH buffering processes' chemical reaction can also potentiate the nerve impulse-blocking action on peripheral nerves.

Embodiments of the present invention will not require a significant deviation from the processes that are currently employed to hypodermically deliver a dose of local anesthetic to the patient or any change to the aspirating syringes and anesthetic cartridges already used as it is designed to replace only the disposable hypodermic needle normally attached to the aspirating syringe by substituting the admixing needle capable of buffering the anesthetic preparation.

It is well known that local anesthetics like Lidocaine work more quickly and with a more profound effect if they are administered at the same pH as the patient's body and that mixing the preparation too far in advance will lead to precipitation and other deleterious effects to the mixed (buffered) preparation. By facilitating the buffering right at the point of use (on demand) within the admixing needle, these unwanted effects can be mitigated without prohibitive expense, extra effort, and/or time penalty. The science of dental and/or medical anesthetic buffering is a component of the embodiments.

One of the most frequently used local anesthetics is 2% Lidocaine with 1:100,000 epinephrine. Lidocaine is a weak base that can precipitate in water over time. To increase shelf life and stability, hydrochloric acid (strong acid) and sodium hydroxide (strong base) are used to adjust the pH to 3.5-5.5.

Human physiologic pH is around 7.4, therefore Lidocaine with epinephrine is approximately 1,000 times more acidic than subcutaneous tissue.

The anesthetic solution is H2O, 2% Lidocaine hydrochloride by weight, 0.002% epinephrine by weight, and trace amounts of sodium hydroxide and/or hydrochloric acid, citric acid, and sodium metabisulfite.

Due to the low pH of the anesthetic solution, the majority of Lidocaine molecules are attached to positive hydrogen ions. These ionized Lidocaine molecules cannot pass through the hydrophobic lipid bilayer of the nerve axon. The body must naturally buffer the anesthetic to a pH of around 7.4 before it can enter the sensory nerve and take effect. This buffering is accomplished by natural bicarbonate ions in the bloodstream produced as a biproduct of CO2 during respiration.

Nevertheless, the natural buffering process is widely different between patients and leads to inconsistent onset times for local anesthesia to be effective. The acidity also increases inflammation and pain in and around the tissues near the injection site during and after the hypodermic injection.

One solution to these problems is to raise the pH of the anesthetic immediately before injection by the addition of a common buffering agent, 8.4% sodium bicarbonate. The ratio of 2% Lidocaine with 1:100,000 epinephrine to 8.4% sodium bicarbonate is 10:1. Therefore a dental cartridge of 1.8 ml is buffered with 0.18 mL of 8.4% sodium bicarbonate.

The buffering occurs according to the following chemical equation:

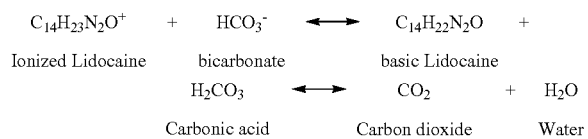

The amount of basic, non-ionized Lidocaine is increased 6000 times. This form is able to cross the lipid bilayer of the sensory nerve axon readily. However, in order to block the sodium channels of the nerve and inhibit signal transduction, the Lidocaine must become ionized again with the addition of a H+ cation. Carbon dioxide is produced as a biproduct of the buffering operation chemical reaction.

This increased concentration of carbon dioxide can readily cross the axon membrane where it facilitates the reverse reaction with the end product of ionized Lidocaine. Thus, carbon dioxide greatly enhances the anesthetic effect of the Lidocaine. Carbon dioxide also potentiates the action of local anesthetics by the direct depressant effect of CO2 on the sensory nerve axon and by concentrating local anesthetic inside the nerve trunk via diffusion trapping.

The cell membrane, also known as the plasma membrane or cytoplasmic membrane, is a biological membrane that separates the interior of all cells from the outside environment (the extracellular space). It consists of a lipid bilayer with embedded proteins.

The basic function of the cell membrane is to protect the cell from its surroundings. The cell's membrane controls the movement of substances in and out of the cell. In this way, it is selectively permeable to ions and organic molecules and most receptive to the passage of ones of the correct pH. This is a crucial fact relating to the usefulness of the present invention Once inside, the sensory nerve cell with the local anesthetic applied will be in equilibrium with the formation of the pronated (ionized) form which does not readily pass back out of the cell and is referred to as ion trapping. In the pronated form, the molecule binds to the local anesthetic binding site on the inside of the ion channel near the cytoplasmic end. To get to the internal surface of the membrane, the drug must penetrate the cell membrane which is achieved best in the non-ionized form and at the same pH as the human body.

A biochemical cascade (signaling cascade or signaling pathway) is a series of chemical pathways which are initiated by stimuli. A nociceptor is a sensory neuron that responds to damaging or potentially damaging stimuli by sending "possible threat" signals to the brain via the spinal cord. If the brain thinks the threat is credible, it creates the sensation of pain to direct attention to the body part, so the threat can hopefully be mediated.

The proteins that detect stimuli are called receptors or sensors. The changes elicited by ligand binding (or signal sensing) in a receptor give rise to a signaling cascade, which is a chain of biological events along a signaling pathway to the brain.

A nerve is an enclosed, cable-like bundle of axon (nerve) fibers and make up the long and slender projections of neurons in the peripheral nervous system. A nerve provides a common pathway for the electrochemical nerve impulses that are transmitted along each of the axons to peripheral organs and the brain. These processes take place in the presence of stimuli.

In neurons, also known as a nerve cells, are electrically excitable cells that receive, process, and transmit information through electrical and chemical signals. The factors that influence the membrane potential are diverse. They include numerous types of ion channels, some of which are chemically gated and some of which are voltage gated. Because voltage-gated ion channels are controlled by the membrane potential, while the membrane potential itself is influenced by these same ion channels, feedback loops that allow for complex temporal dynamics arise, including oscillations and regenerative events such as action potentials.

Transduction proteins form or connect to miniscule pathways called ion channels through which charged particles called ions, like sodium or potassium, enter the cell. This movement of the charged particles creates the electrical signals. Each electrical signal spreads along the length of the cell by means of other proteins which also form ion channels ultimately culminating in the release of a chemical neurotransmitter. The next neuron receives the neurotransmitter via other receptor proteins, which also are themselves ion channels or coupled to, ion channels.

Electrical signals within biological organisms are, in general, driven by ions. Ions cross the cell membrane under influences: diffusion and electric fields. A simple example wherein two solutions—A and B—are separated by a porous barrier illustrates that diffusion will ensure that they will eventually mix into equal solutions. This mixing occurs because of the difference in their concentrations. The region with high concentration will diffuse out toward the region with low concentration. If, however, the porous barrier is selective to which ions are let through, then diffusion alone will not determine the resulting solution.

Returning to the previous example, let's construct a barrier that is permeable only to sodium ions. Now, only sodium is allowed to diffuse cross the barrier from its higher concentration in solution A to the lower concentration in solution B. This will result in a greater accumulation of sodium ions than chloride ions in solution B and a lesser number of sodium ions than chloride ions in solution A.

This means that there is a net positive charge in solution B from the higher concentration of positively charged sodium ions than negatively charged chloride ions. Likewise, there is a net negative charge in solution A from the greater concentration of negative chloride ions than positive sodium ions. Since opposite charges attract and like charges repel, the ions are now also influenced by electrical fields as well as forces of diffusion. Therefore, positive sodium ions will be less likely to travel to the now-more-positive B solution and remain in the now-more-negative A solution. The point at which the forces of the electric fields completely counteract the force due to diffusion is called the equilibrium potential. At this point, the net flow of the specific ion (in this case sodium) is zero.

The resistance of a pure lipid bilayer to the passage of ions across it is very high, but structures embedded in the membrane can greatly enhance ion movement, either actively or passively, via mechanisms called facilitated transport and facilitated diffusion. The two types of structure that play the largest roles are ion channels and ion pumps, both usually formed from assemblages of protein molecules. Ion channels provide passageways through which ions can move. In most cases, an ion channel is permeable only to specific types of ions (for example, sodium and potassium but not chloride or calcium), and sometimes the permeability varies depending on the direction of ion movement. Ion pumps, also known as ion transporters or carrier proteins, actively transport specific types of ions from one side of the membrane to the other, sometimes using energy derived from metabolic processes to do so.

Ligand-gated ion channels are channels whose permeability is greatly increased when some type of chemical ligand at the correct pH binds to the protein structure.

As an action potential (nerve impulse) travels down an axon, there is a change in polarity across the membrane of the axon. In response to a signal from another neuron, sodium—(Na+) and potassium—(K+) gated ion channels open and close as the membrane reaches its threshold potential. Na+ channels open at the beginning of the action potential, and Na+ moves into the axon, causing depolarization. Repolarization occurs when the K+ channels open and K+ moves out of the axon, creating a change in polarity between the outside of the cell and the inside. The impulse travels down the axon in one direction only, to the axon terminal where it signals other neurons.

Transmembrane proteins can also serve as ligand transport proteins that alter the permeability of the cell's lipid bilayer membrane to small molecules and ions. The membrane alone has a hydrophobic core through which polar or charged molecules cannot diffuse. Membrane proteins contain internal channels that allow such molecules to enter and exit the cell. Many ion channel properties are specialized to select for only a particular ion; for example, potassium and sodium channels often discriminate for only one of the two ions. Most ligands are soluble molecules from the extracellular medium which bind to cell surface receptors.

Ion pumps are integral membrane proteins that carry out active transport, i.e., use cellular energy to "pump" the ions against their concentration gradient. Such pumps take in ions from one side of the membrane (decreasing the concentration there) and release them on the other side (increasing their concentration there).

The ion pump most relevant to the action potential is the sodium-potassium pump which transports three sodium ions out of the cell and two potassium ions in. As a consequence, the concentration of potassium ions K+ inside the neuron is roughly 20-fold larger than the outside concentration, whereas the sodium concentration outside is roughly nine-fold larger than inside. In a similar manner, other ions have different concentrations inside and outside the neuron, such as calcium chloride and magnesium.

If the numbers of each type of ion were equal, the sodium-potassium pump would be electrically neutral, but, because of the three-for-two exchange, it gives a net movement of one positive charge from intracellular to extracellular for each cycle, thereby contributing to a positive voltage difference. The pump has three effects: (1) it makes the sodium concentration high in the extracellular space and low in the intracellular space; (2) it makes the potassium concentration high in the intracellular space and low in the extracellular space; (3) it gives the intracellular space a negative voltage with r espect to the extracellular space.

The sodium-potassium pump is relatively slow in operation. If a cell were initialized with equal concentrations of sodium and potassium everywhere, it would take hours for the pump to establish equilibrium. The pump operates constantly but becomes progressively less efficient as the concentrations of sodium and potassium available for pumping are reduced.

Ion pumps influence the action potential only by establishing the relative ratio of intracellular and extracellular ion concentrations. The action potential involves mainly the opening and closing of ion channels not ion pumps. In particular, ion pumps play no significant role in the repolarization of the membrane after an action potential.

Most channels are specific (selective) for one ion; for example, most potassium channels are characterized by 1000:1 selectivity ratio for potassium over sodium, though potassium and sodium ions have the same charge and differ only slightly in their radius. The channel pore is typically so small that ions must pass through it in single-file order. Channel pores can be either open or closed for ion passage, although several channels demonstrate various sub-conductance levels. When a channel is open, ions permeate through the channel pore down the transmembrane concentration gradient for that particular ion. The rate of ionic flow through the channel, i.e. single-channel current amplitude, is determined by the maximum channel conductance and electrochemical driving force for that ion, which is the difference between the instantaneous value of the membrane potential and the value of the reversal potential.

A channel may have several different states (corresponding to different conformations of the protein), but each such state is either open or closed. In general, closed states correspond either to a contraction of the pore—making it impassable to the ion—or to a separate part of the protein, stoppering the pore. For example, the voltage-dependent sodium channel undergoes inactivation, in which a portion of the protein swings into the pore, sealing it. This inactivation shuts off the sodium current and plays a critical role in the action potential.

Ion channels can be classified by how they respond to their environment. For example, the ion channels involved in the action potential are voltage-sensitive channels; they open and close in response to the voltage across the membrane. Ligand-gated channels form another important class; these ion channels open and close in response to the binding of a ligand molecule, such as a neurotransmitter. Other ion channels open and close with mechanical forces. Still other ion channels such as those of sensory neurons open and close in response to other stimuli, such as light, temperature or pressure.

In the brain, in almost every neuron, are other ion channel proteins—particularly sodium channels, which start the action potentials (by letting sodium ions into the neuron) and potassium channels, which end action potentials (by letting potassium ions out of a neuron).

In physiology, an action potential occurs when the membrane potential of a specific axon location rapidly rises and falls. This depolarization then causes adjacent locations to similarly depolarize. Action potentials occur in several types of cells, called excitable cells, which include neurons.

Action potentials are generated by special types of voltage-gated ion channels embedded in a cell's plasma membrane. These channels are shut when the membrane potential is near the (negative) resting potential of the cell, but they rapidly begin to open if the membrane increases to a precisely defined threshold voltage, depolarizing the transmembrane potential. When the channels open, they allow an inward flow of sodium ions, which changes the electrochemical gradient, which in turn produces a further rise in the membrane potential. This then causes more channels to open, producing a greater electric current across the cell membrane, and so on. The process proceeds explosively until all the available ion channels are open, resulting in a large upswing in the membrane potential.

The rapid influx of sodium ions causes the polarity of the plasma membrane to reverse, and the ion channels then rapidly inactivate. As the sodium channels close, sodium ions can no longer enter the neuron, and then they are actively transported back out of the plasma membrane. Potassium channels are then activated, and there is an outward current of potassium ions, returning the electrochemical gradient to the resting state. After an action potential has occurred, there is a transient negative shift, called the afterhyperpolarization.

Signaling molecules interact with a target cell as a ligand-to-cell surface receptor, and/or by entering the cell through its membrane or endocytosis for intracrine signaling this results in the activation of second messengers, leading to various physiological effects most commonly protein phosphorylation catalyzed by response.

The cell membrane, or plasma membrane, is a biological membrane that surrounds the cytoplasm of the cell wall. The membrane separates and protects the cell from its surrounding environment. It is mostly made up of a double layer of phospholipids, which are amphiphilic, partly hydrophobic and partly hydrophilic. It is also called a fluid mosaic membrane. Embedded within this membrane is a variety of protein molecules acting as channels and pumps that move various molecules in and out of the cell.

The intermediate space is located between the outer and inner membrane. It is also called the pepmitochondial space and is freely permeable to small molecules. The concentration of small molecules, such as ions and sugars, is the same as in the cytosol or intracellular fluid also known as the cytoplasmic matrix.

Larger proteins must have a specific signaling sequence to be transported across the outer membrane, so protein composition of this space is different than the cytosol. Cells consist of cytoplasm enclosed within a membrane which contains many biomolecules such as proteins and nucleic acids.

Extracellular fluid denotes body fluid outside of cells. Extracellular fluid provides the medium for the exchange of substances between the extracellular fluid and the cells. This normally takes place by dissolving, mixing, and transporting in the fluid medium. This is where the local anesthetic is deposited hypodermically via the admixing needle injection and a crucial fact related to the usefulness of the invention.

There is a significant difference between the concentrations of sodium and potassium ions inside and outside the cell. Sodium ion content in extracellular fluid is considerably higher and this is conversely true of the potassium ion concentrations inside of the cells. These differences cause all cell membranes to be electrically charged with the positive charge located on the outside of the cell. In a resting neuron the potential is about −70 mV (when not conducting an impulse).

Voltage-gated ion channels in the cell membrane can be temporarily opened under specific circumstances to allow a brief inflow of sodium ions into the cell. This is due to the sodium ion concentration gradient that exists between the outside and the inside of the cell, which causes the cell to temporarily depolarize (lose its electrical charge) forming the basis of action potentials.

Lidocaine is one local anesthetic that binds preferentially to the inactive state of the voltage-gated sodium channels but has also been found to bind to potassium channels, G-protein coupled receptors, NMDA receptors, and calcium channels which are all part of the nerve signal transmission process within the central nervous system.

Two special classes of protein deal with the ionic gradients found across cellular and sub-cellular membranes in nature called ion channels and ion pumps. Both pumps and channels are integral membrane proteins that pass through the bilayer, but their roles are quite different. Ion pumps are the proteins that build and maintain the chemical gradients by utilizing an external energy source to move ions against the concentration gradient to an area of higher chemical potential. Alternatively, the energy source can be another chemical gradient already in place. It is through the action of ion pumps that cells are able to regulate pH via the pumping of protons.

In contrast to ion pumps, ion channels do not build chemical gradients but rather dissipate them in order to perform work or send a signal. Probably the most familiar and best studied example is the voltage-gated Na+ channel, which allows conduction of an action potential along neurons. All ion pumps have some sort of trigger or "gating" mechanism. In the previous example it was electrical bias, but other channels can be activated by binding a molecular agonist or through a conformational change in another nearby protein.

Ligands are termed first messengers, while receptors are the signal transducers which then activate primary effectors. Such effectors are often linked to second messengers, which can activate secondary effectors, and so on. First messengers are signaling molecules that reach the cell from extracellular fluid and bind to specific receptors.

Second messengers are substances that enter the cytoplasm and act within the cell to trigger a response. As an electrical signal reaches a threshold voltage level and so propagates along its length, the cell opens sodium channels to allow the influx of sodium ions. These sodium channels are proteins (poly-amino acids) that sit across the membrane that forms the surface of the nerve. This protein folds into a cylindrical shape with a central channel that can be the nerve cell.

Most signal transduction pathways involve the binding of signaling molecules (ligands) to receptors that trigger events inside of the cell. Activation energy is the minimum energy required to start a chain reaction.

Extracellular receptors are integral transmembrane proteins and make up the greater percentage of these receptors.

They span the plasma membrane of the cell, with one part of the receptor on the outside and one on the inside. Ligands bind to the part which is outside the cell which induces a change in the configuration of the inside part. This is called receptor activation. This either results in the activation of an enzyme domain of the receptor or the exposure of the binding site for other intracellular signaling proteins within the cell, eventually propagating the signal through the cytoplasm.

The lipid bilayer (or phospholipid bilayer) is a thin polar membrane made of two layers of lipid molecules. These membranes are flat sheets that form a continuous barrier around all cells. The cell membranes of almost all living organisms and many viruses are made of a lipid bilayer, as are the membranes surrounding the cell nucleus and other sub-cellular structures. The lipid bilayer is the barrier that keeps ions, proteins and other molecules where they are needed and prevents them from diffusing into areas where they should not be. Lipid bilayers are ideally suited to this role, even though they are only a few nanometers in width, they are impermeable to most water-soluble (hydrophilic) molecules. Bilayers are particularly impermeable to ions, which allows cells to regulate salt concentrations and pH by transporting ions across their membranes using proteins called ion pumps.

Lipid bilayers are also involved in signal transduction through their role as the home of integral membrane proteins.

Lipid kinases phosphorylate lipids in the cell, both on the plasma membrane as well as on the membranes of the organelles. The addition of phosphate groups can change the reactivity and localization of the lipid and can be used in signal transmission.

Some local anesthetic preparations also contain a vasoconstrictor like epinephrine to control bleeding and prolong the anesthetic effect by reducing blood-flow to and from the area which is responsible for the body's normal expulsion of the preparation which ends the local anesthetic effect and usefulness. Buffering the solution will have no deleterious effect on these preparations or to the patient. The buffered solution will be removed during the body's normal excretion process which is responsible to remove xenobiotics (foreign molecules) thereby ending the local anesthesia event albeit much more slowly.

The admixing needle is practical for dental or medical local anesthetic preparation buffering but not limited to such uses and could also involve point of use mixing of gels, liquids, or gasses or chemically activated epoxies or glues that would set up or harden if mixed together too far in advance.

Figure 16:
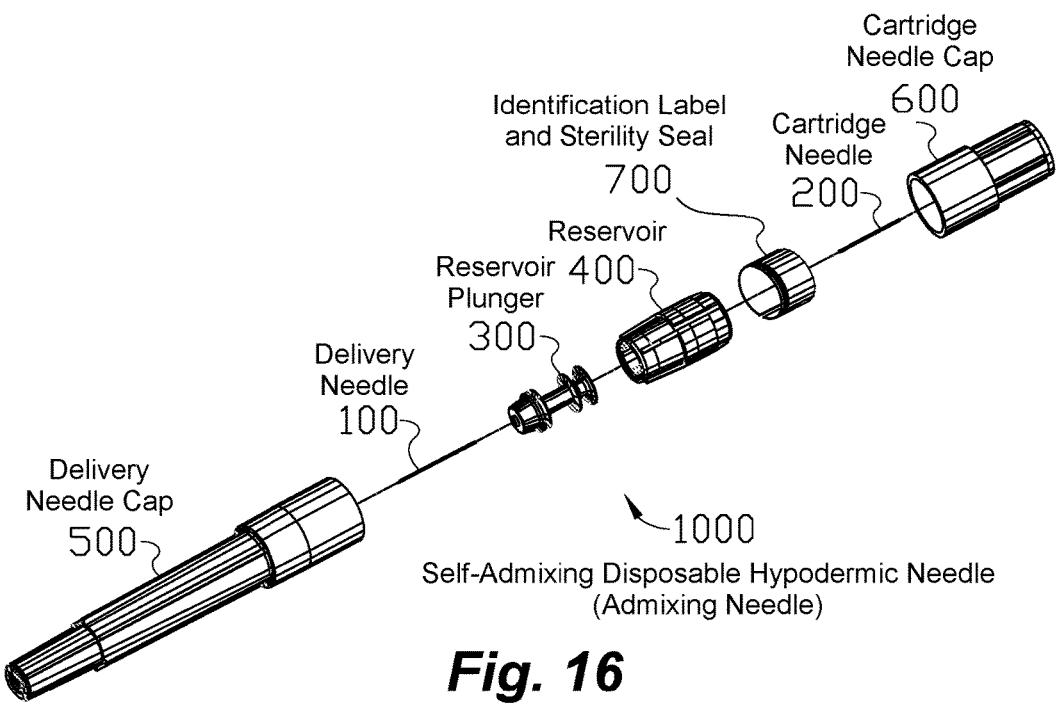
FIG. 16 is an exploded isometric view of the admixing needle showing its individual components.
Figure 17:
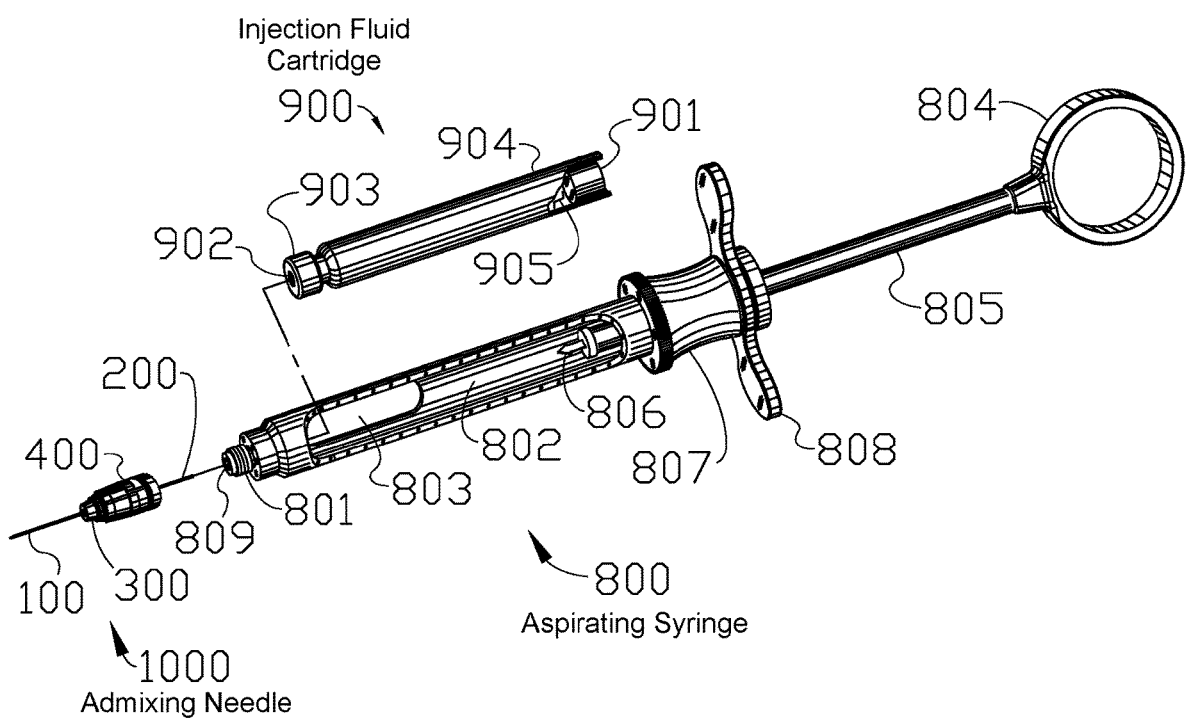
FIG. 17 is an isometric view of the syringe with the admixing needle and injection fluid cartridges shown displaced.

Referring now to the figures which depict an apparatus and process for homogeneous admixing of two or more constituents into a final preparation on demand. The apparatus is referred to as the admixing needle 1000, which includes a delivery needle 100, cartridge needle 200, male body (reservoir plunger) 300, female body (reservoir) 400, delivery needle cap 500, cartridge needle cap 600, and an identification label and sterility seal 700, as shown in FIG. 16. In this example, the reservoir contains a predetermined volume of an 8.4% solution of sodium bicarbonate neutralizing (buffering) solution or other admixing constituent to facilitate homogeneous mixing when conjoined with a syringe. In the example, the syringe is an aspirating syringe 800, which concentrically predisposes and maintains the mechanical position of an injection fluid cartridge 900, as shown in FIG. 17. In this example, the injection fluid cartridge 900 contains the local anesthetic Lidocaine, and the reservoir 400 of the admixing needle 1000 contains sodium bicarbonate to buffer (alkalize) the Lidocaine by mixing the two liquids together. The mixing initially occurs by forcing the additive in the female body (reservoir) 400 into the injection fluid cartridge 900 to create an injection mixture within the injection fluid cartridge 900. Additional mixing occurs when the syringe is operated to force the injection mixture from the injection fluid cartridge 900 back out through the admixing needle 1000, which homogeneously mixes the injection fluid with the additive immediately prior to delivery to the patient via hypodermic injection.

The process begins with the dentist or medical practitioner inserting the injection fluid injection fluid cartridge 900 into the cartridge port 802 of the syringe 900, as shown in FIG. 17, with the cartridge diaphragm 902 and the cartridge metal diaphragm clamp 903 facing the anterior end of the syringe 800. The practitioner retracts the syringe plunger 805 by placing their thumb into the syringe thumb ring 804 and, while gripping the syringe finger grip 807 on the anterior side of the syringe finger bar 808, moving the syringe plunger 805 posteriorly to create a bit of space between the cartridge 900 and the harpoon barb 806, which is predisposed on the end of the syringe plunger 805. The posterior end of the syringe thumb ring 804 is then sharply struck with the palm to set the harpoon barb 806 into the cartridge stopper 901, which is predisposed at the posterior end of the injection fluid cartridge glass body 904.

Figure 2:
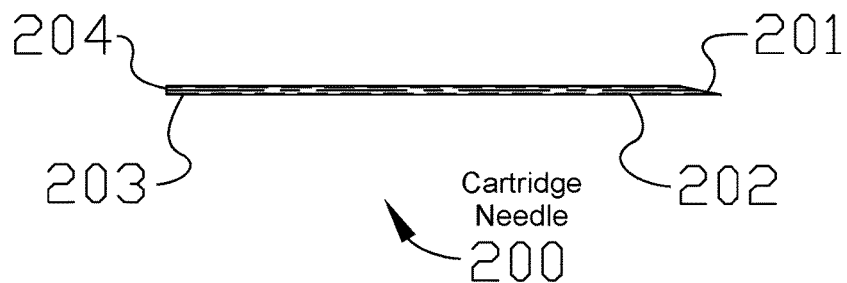
FIG. 2 is a side view of a cartridge needle on the admixing needle.
Figure 7:
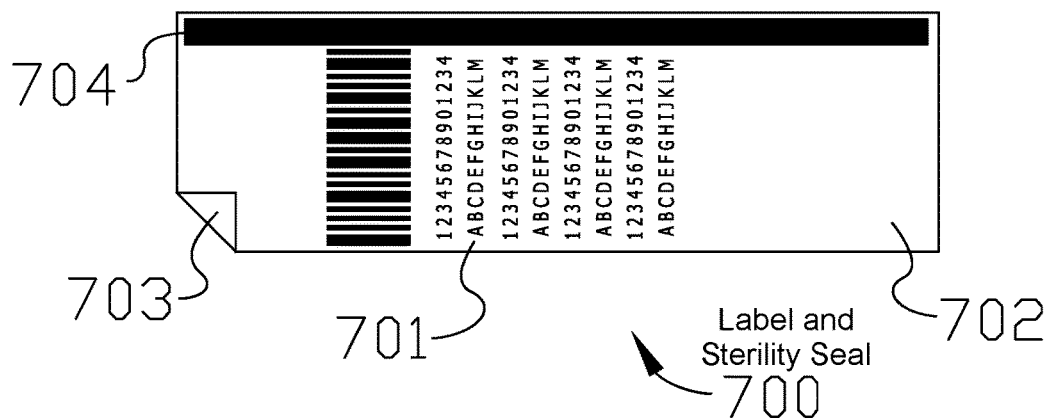
FIG. 7 is a conceptual illustration of an identification label and sterility seal on the admixing needle.

The previous steps of the local anesthetic injection procedure are identical to the currently followed procedure. The correct length and gage of the admixing needle 1000, is selected for the intended injection required by reviewing the identification label and sterility seal 700, which is located across the cartridge needle cap label area 602, and the delivery needle cap label area 502, as shown in FIG. 16, which incorporates human and/or machine readable identification label markings 701. In this example, the label 700 also includes an Identification label base color 702, identification label colored stripe 704, and held on with identification label sterility adhesive 703, as shown in FIG. 7. The cartridge needle cap 600, as shown in FIG. 6, is removed from the admixing needle 1000, and set aside exposing the cartridge needle cap chamfer 604, which is used to coaxially align it to the syringe 800. The female body (reservoir) 400 incorporates a female body cartridge needle receiver 402, as shown in FIG. 4, into which is embedded a cartridge needle blunt end 203, on a cartridge needle 200, containing a cartridge needle lumen 204, which is a hollow pathway for fluid to bidirectionally flow as shown in FIG. 2, and secured to the female body (reservoir) 400 with female body needle adhesive 410.

The cartridge needle bevel point end 201, located on the posterior end of the admixing needle 1000, is coaxially aligned with a needle access lumen 809 of the syringe 800 which receives the cartridge needle 200. The admixing needle 1000 is attached to the syringe 800 by placing the female body chamfered lead-in 409, and female body female threaded area 408, over the syringe male threaded area 801, and rotating the admixing needle 1000 clockwise to tighten, as shown in FIG. 17, by gripping it by the delivery needle cap external spline 505. The female body external female groove 406 is a longitudinally displaced feature that accepts the delivery needle cap internal spline 501, which is a longitudinally displaced feature which only allows the delivery needle cap 500, to move longitudinally relative to the female body (reservoir) 400, and directly transfer the clockwise radial tightening force. This ensures ingress of the cartridge needle bevel point 201 into the injection fluid cartridge diaphragm 902, which is made of an elastomeric material that seals around the exterior periphery of the cartridge needle body 202.

In its initial position, the relationship of the male body first seal ring 302, which is a thin, circular, male feature on the male body (reservoir plunger) 300, interacts with the internal surface of the female body cavity 401, which is smooth, to create a piston effect by deflecting slightly anteriorly to maintain proper contact pressure with the inside diameter. The male body (reservoir plunger) 300, geometry and relative linear position to the female body cavity 401, within the female body (reservoir) 400, creates a known volume of additive, in this example a solution of 8.4% liquid sodium bicarbonate. Varying the dimensions of these component parts will allow for different volumes of additives as well as the prepositioning of the male body (reservoir plunger) 300 within the female body (reservoir) 400. The delivery needle cap 500 is then moved posteriorly towards the syringe 800, along the female body external female groove 406 and the female body external male spline 407, thereby engaging the delivery needle cap internal conical area 503 with the male body tapered nose 306, which transfers the liner force and posteriorly translates the male body (reservoir plunger) 300 toward and into the female body (reservoir) 400. This excises the additive in the reservoir 400, in the example liquid sodium bicarbonate, posteriorly through the female body cartridge needle receiver 402, through the cartridge needle lumen 204, through the cartridge needle 200, and into the reservoir area 905 of the injection fluid cartridge 900 to begin the mixing process.

As the male body second seal ring 303, which is a thin, circular, male feature on the male body (reservoir plunger) 300, interacts with the female body end ring snap lock 405, on the female body (reservoir) 400, an audible and tactile "click" indication is given to the dentist or medical practitioner. As the male body third seal ring 304, which is a thin, circular, male feature on the male body (reservoir plunger) 300, interacts with the female body end ring snap lock Indicator 405, on the female body (reservoir) 400, an audible and tactile "click" indication is given to the dentist or medical practitioner and the male body insertion stop surface 308, comes into contact with the anterior end of the female body (reservoir) 400, to stop the ingress of the male body (reservoir plunger) 300, into the female body cavity 401, which also irreversibly locks the two together. At the end of the ingress travel of the male body (reservoir plunger) 300 into the female body (reservoir) 400, the male body first seal ring 302 passes through the female body fluid bypass groove 404, which is an undercut feature on the inside wall of the female body cavity 401 on the female body (reservoir) 400. This provides a fluid ingress and egress path between the injection fluid cartridge 900, and the male body needle receiver 301, in which the delivery needle blunt end 103 is affixed with the male body needle adhesive 309. This coaxially aligns the delivery needle body 102, having a delivery needle lumen 104, and a delivery needle bevel point 101 that interacts with the patient when the local anesthetic is hypodermically administered through the stratified squamous epithelium tissues to the proximity of the nerve requiring local anesthesia via the admixing needle 1000.

After the dentist or medical practitioner positions the delivery needle bevel point 101 of the admixing needle 1000 to the approximate position within the patient's tissue, the syringe thumb ring 804 is moved posteriorly to determine if the delivery needle bevel point 101 is positioned within a vein or artery by looking through the syringe cartridge port 802, or the syringe view port 803, to see if blood has been withdrawn into the reservoir area 905 of the injection fluid cartridge 900, which would be visible through the cartridge glass body 904. This withdrawing action creates a negative pressure area (vacuum) within the cartridge reservoir area 905, which also brings any residual vestige of the additive solution left in the female body cavity 401, or the cartridge needle lumen 204, into the injection fluid cartridge 900.

If the delivery needle bevel point 101 is correctly positioned, the dentist or medical practitioner then moves the syringe thumb ring 804 anteriorly towards the injection fluid cartridge 900, which in turn moves the cartridge stopper 901 anteriorly thus decreasing the volume within the injection fluid cartridge 900. This, in turn, increases the pressure on the injection mixture forcing it out the only egress path available, which is the cartridge needle lumen 204. This lumen is in axial communication with a mixing surface of the female body, in this example the mixing rings 403, until it interacts with a mixing surface of the male body, in this example the mixing rings 305, which are geometric features of both male (reservoir plunger) and female (reservoir) parts that direct and redirect the flow of the preparation in a radially and outwardly direction across them which creates vortices and turbulence responsible to effect the homogeneous mixing. The preparation also moves around the male body first seal ring 302, passes through the female body fluid bypass groove 404, and down through the male body intersecting fluid pathway 307, which has fluid communication with the male body needle receiver 301, in which the delivery needle blunt end 103, is affixed with male body needle adhesive 309, which coaxially aligns the delivery needle body 102, having a delivery needle lumen 104, and a delivery needle bevel point 101, which finally interacts with the patient. The delivery needle 100 is removed from the patient and, if additional local anesthetic placement is required and there is still some injection mixture (in this example buffered Lidocaine) left in the cartridge, the delivery needle can be repositioned within the stratified squamous epithelium tissues to the proximity of a different nerve repeating the aspiration step to test for mispositioning within the venous or arterial system.

If correctly positioned, the balance or required amount of the injection mixture can be administered. After removing the admixing needle 1000 from the patient, the delivery needle cap 500 is replaced over the delivery needle 100 to prevent accidental contaminated needle sticks. The admixing needle 1000 can then be removed from the syringe male threads 801 by rotating the delivery needle cap 500 counterclockwise to unseat it. The cartridge needle 200 can then be covered with the cartridge needle cap 600 and the admixing needle properly discarded. The used injection fluid cartridge 900 is removed from the syringe 800 and disposed of properly. If additional injection mixture is needed to completely facilitate the local anesthesia effect necessary to permit the painful procedure, the entire procedure is repeated as many times as is required up to the maximum legal dosage.

Figure 18A:
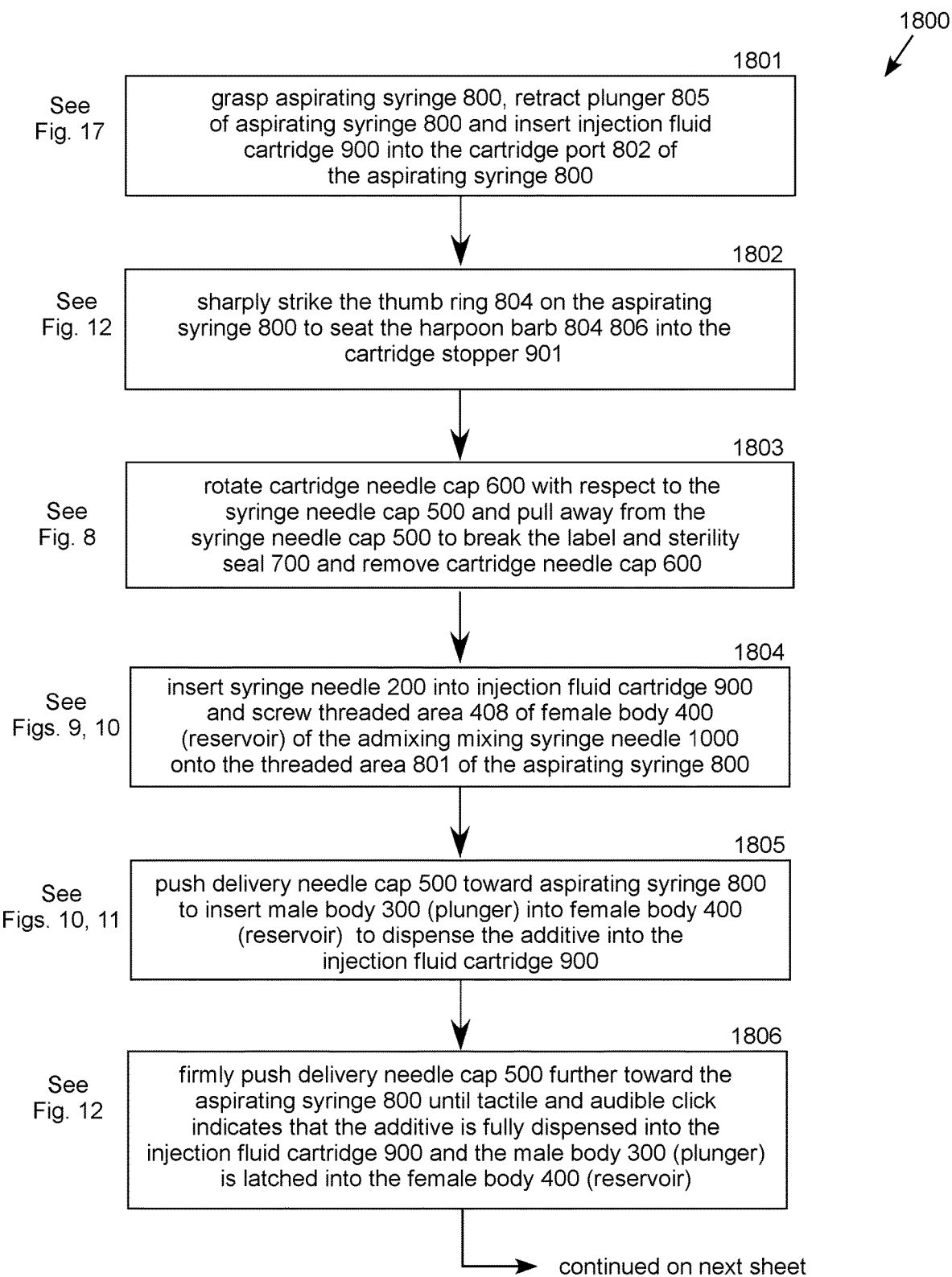
FIGS. 18A-18B depict a logic flow diagram of a procedure for using the syringe and Injection fluid cartridge, in conjunction with the admixing needle.
Figure 18B:
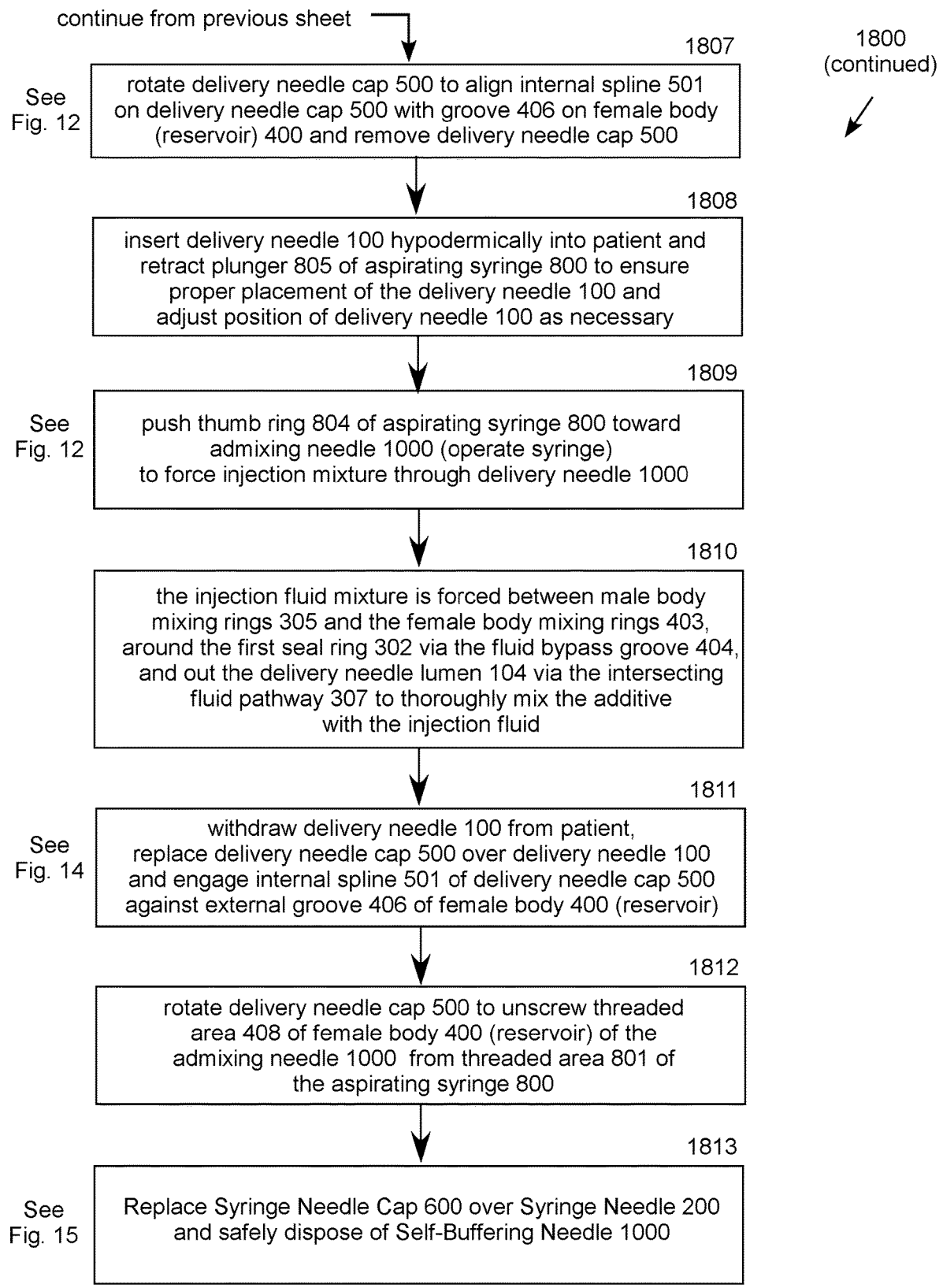

FIGS. 18A-18B depict a logic flow diagram 1800 of a procedure for using the aspirating syringe 800 and the injection fluid cartridge 900 in conjunction with the admixing needle 1000. In this example, the injection fluid is Lidocaine, the additive is sodium bicarbonate, resulting buffered Lidocaine as the injection mixture. The procedure can be performed by a syringe user, such as dentist, physician, veterinarian, technician, medical practitioner, and so forth. While the admixing needle 1000 is specifically designed for use with the aspirating syringe 800 by a dental or medical professional, it may find use in other settings in which the admixing needle 1000 is used with an aspirating syringe or other suitable type of syringe by humans or machines.

In step 1801, the user grasps the aspirating syringe 800 and retracts the syringe plunger 805 of the aspirating syringe 800 and inserts a cartridge containing an injection fluid, in this example a Lidocaine cartridge 900, into the cartridge port 802 of the aspirating syringe 800. See FIG. 17.

Figure 12:
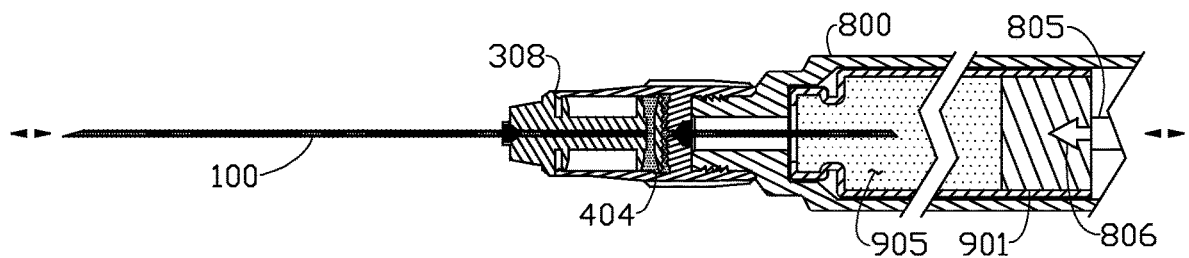
FIG. 12 is a sectional side view of the admixing needle fully attached to the syringe with the male body (reservoir plunger) latched into the female body (reservoir) which positions these two components to activate the fluid bypass groove valve enabling bi-directional fluid flow which allows the injection mixture (in this example Lidocaine buffered with sodium bicarbonate) to be excised from the cartridge located within the syringe anteriorly through the delivery needle on the admixing needle.
Figure 13:
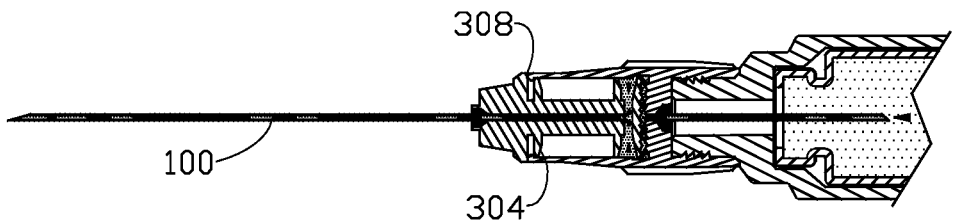
FIG. 13 is a sectional side view of the admixing needle fully attached to the syringe with the injection mixture partially injected from the syringe through the admixing needle.

Step 1801 is followed by step 1802, in which the user grasps the aspirating syringe 800 with one hand and sharply strikes the posterior end of the thumb ring 804 on the aspirating syringe 800, which seats the syringe harpoon barb 806 located on the anterior end of the syringe plunger 805 into the posterior end of the Lidocaine cartridge stopper 901 located at the posterior end of the Lidocaine cartridge 900. See FIG. 12.

Figure 8:
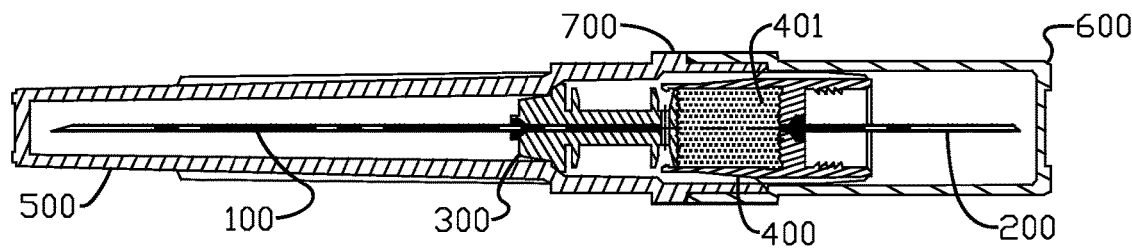
FIG. 8 is a sectional side view of the admixing needle in the "as shipped" (pre-use) condition.

Step 1802 is followed by step 1803, in which the user rotates the cartridge needle cap 600 with respect to the delivery needle cap 500, and pulls the cartridge needle cap 600 linearly away from the delivery needle cap 500 to break the identification label and sterility seal 700 and removes the cartridge needle cap 600. See FIG. 8.

Figure 9:
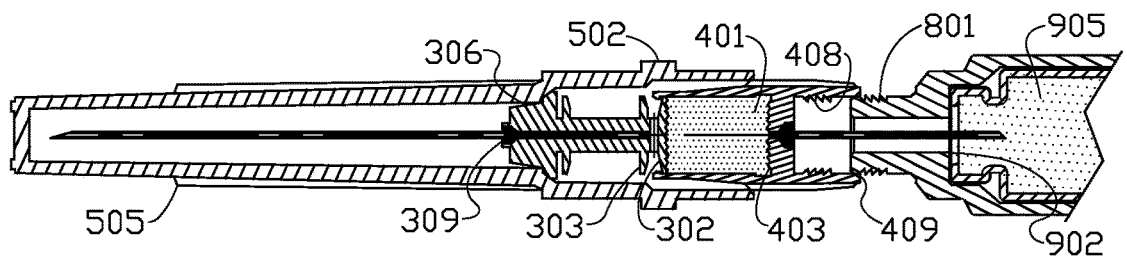
FIG. 9 is a sectional side view of the admixing needle with the delivery needle cap removed in the process of being attached to a syringe.
Figure 10:
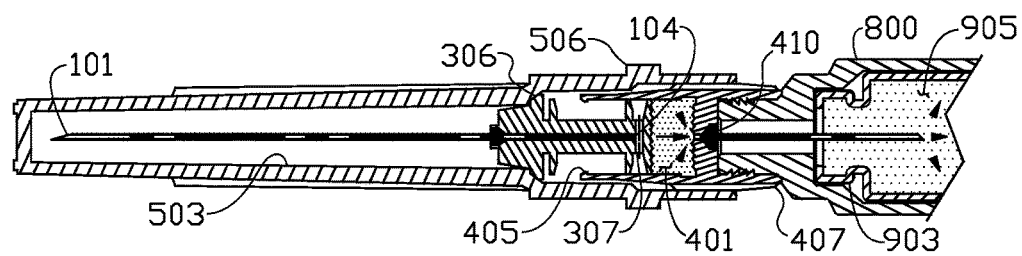
FIG. 10 is a sectional side view of the admixing needle fully attached to the syringe and with the male body (reservoir plunger) partially pushed into the female body (reservoir).

Step 1803 is followed by step 1804, in which the user inserts the cartridge needle 200 into the Lidocaine cartridge 900 through the needle access lumen 809 and screws the female threaded area 408 of the female body (reservoir) 400 of the admixing needle 1000 onto the male threaded area 801 of aspirating syringe 800 fully. See FIGS. 9 and 10.

Figure 11:
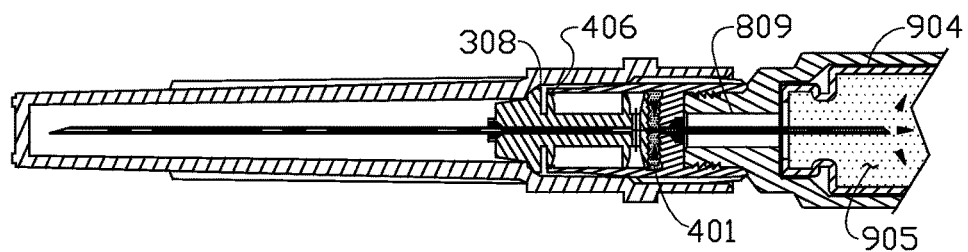
FIG. 11 is a sectional side view of the admixing needle fully attached to the syringe with the male body (reservoir plunger) linearly translated into the female body (reservoir) to a position just before latching and fluid bypass groove valve operation whereby only allowing fluid to flow from the admixing needle to the injection fluid cartridge.

Step 1804 is followed by step 1805, in which the user pushes the delivery needle cap 500 posteriorly towards the aspirating syringe 800 to linearly translate the male body (reservoir plunger) 300 into the female body (reservoir) 400 to begin to excise the buffering agent into Lidocaine cartridge 900. See FIGS. 10 and 11.

Step 1805 is followed by step 1806, in which the user firmly pushes the delivery needle cap 500 further towards the aspirating syringe 800 until the user hears and feels a tactile click indicating that the buffering agent has been fully excised into the Lidocaine cartridge 900, at which point the male body (reservoir plunger) 300 is irreversibly latched into female body (reservoir) 400 to create a mixing area between the male body mixing rings 305 on the male body first seal ring 302 and the female body mixing rings 403 on the inside the female body cavity 401. Due to the irreversible latching of the reservoir plunger 300 into the reservoir 400, the admixing needle 1000 can only be used once (single-use) for admixing but, after single-use operation, the admixing needle may still be used as a non-admixing hypodermic needle for the aspirating syringe 800 or another suitable syringe. At this point, the user may shake the aspirating syringe 800 to aid mixing the additive (in this example the buffering agent) with the injection fluid (in the example Lidocaine) within the cartridge 900. This mechanical action helps speed the chemical mixing of the constituents. See FIG. 12.

Step 1806 is followed by step 1807, in which the user rotates the delivery needle cap 500 as far clockwise as possible to align a delivery needle internal male spline with 501 on the inside of the delivery needle cap 500 with a longitudinal groove 406 in the female body (reservoir) 400 and removes the delivery needle cap 500 from the admixing needle 1000. See FIG. 12.

Step 1807 is followed by step 1808, in which the user places the admixing needle 1000 hypodermically into the patient's squamous stratified epithelium tissues and pulls the syringe thumb ring 804 posteriorly to create a vacuum within the Lidocaine cartridge reservoir area 905 which in turn creates a vacuum through the entire admixing needle 1000 to the patient's tissues. If the delivery needle 100 is improperly placed within the venous or arterial system of the patient it will bring blood back through the admixing needle 1000 and into the Lidocaine cartridge 900 which will be visible through the cartridge glass body 904 and the syringe cartridge port 802 or syringe view port 803. Because it is undesirable to inject the Lidocaine which may contain Epinephrine (which is Adrenaline) into a vein or artery, the delivery needle 100 would be withdrawn some amount and or repositioned within the patient's non-venous or non-arterial squamous stratified epithelium tissues.

Step 1808 is followed by step 1809, in which the user pushes the syringe thumb ring 804 of the aspirating syringe 800, which in turn linearly translates the syringe plunger 805 toward the admixing needle 1000 (operates syringe) to excise the injection mixture (in this example buffered Lidocaine) from the Lidocaine cartridge reservoir area 905 within the Lidocaine cartridge glass body 904. See FIG. 12.

Figures 3A, 3B, 3C:
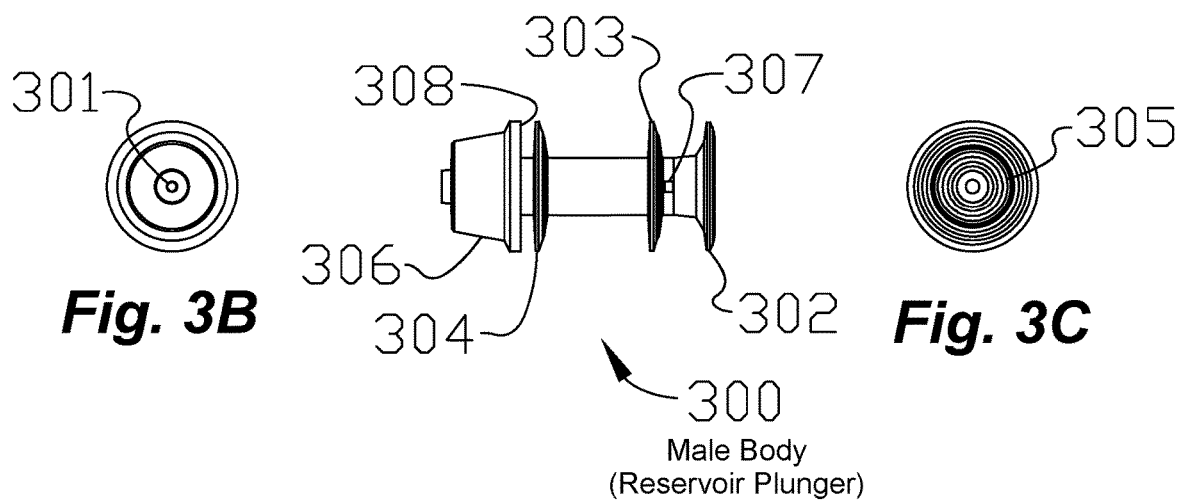
FIGS. 3A-3C include a side view and both orthogonal end views of a male body (reservoir plunger) on the admixing needle.

Step 1809 is followed by step 1810, in which the injection mixture is forced between the mixing rings 305 of the male body (reservoir plunger) 300 and the female body mixing rings 403 inside the female body cavity 401, around the male body first seal ring 302 via the female body fluid bypass groove 404 which make up the valve, and out the delivery needle lumen 104 via the male body intersecting fluid pathway 307 to thoroughly mix the buffered Lidocaine upon delivery to the patient via the delivery needle 100. See FIGS. 3A-3C.

Figure 14:
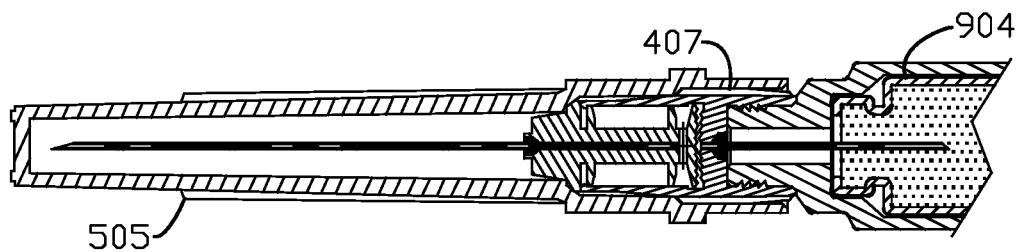
FIG. 14 is a sectional side view of the admixing needle attached to the syringe with the delivery needle cap replaced after use.

Step 1810 is followed by step 1811, in which the user withdraws the delivery needle 100 from the patient and replaces the delivery needle cap 500 over the delivery needle 100 and engages the internal spline 501 of the delivery needle cap 500 against the female body external groove 406 of the female body (reservoir) 400. See FIG. 14.

Step 1811 is followed by step 1812, in which the user rotates the delivery needle cap 500 counterclockwise to unscrew the female body threaded area 408 of the female body (reservoir) 400 of the admixing needle 1000 from the syringe male threaded area 801 of aspirating syringe 800.

Figure 15:
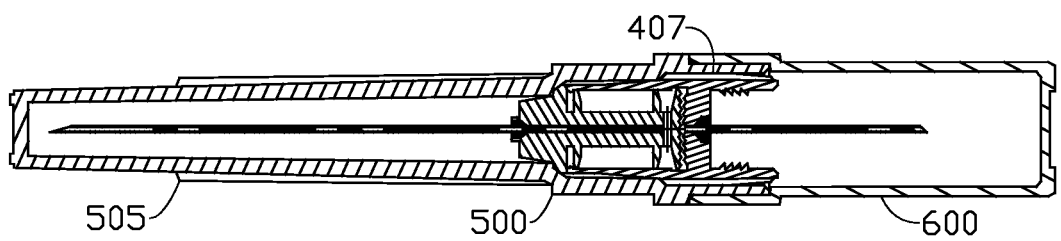
FIG. 15 is a sectional side view of the admixing needle detached from the syringe with the cartridge needle cap replaced and ready for disposal.

Step 1812 is followed by step 1813, in which the user replaces the cartridge needle cap 600 over the cartridge needle 200 and safely disposes of the admixing needle 1000. See FIG. 15.

In the embodiment described above, the illustrative procedure is dental anesthesia administration in which the injection fluid is Lidocaine and the additive is a buffering agent, such as sodium bicarbonate. It will be appreciated, however, that embodiments of the invention may be used for a wide range of procedures and processes involving mixing of an admixing constituent with an injection fluid immediately before dispensing the combined mixture. For example, the embodiments of the invention may include a wide range of dental, medical, veterinarian, industrial and other procedures involving the dispensing of combined mixtures into human, animal, or inanimate subjects and/or objects. The admixing needle may work with any type of syringe, and is well suited to working with the type of aspirating syringe commonly used to inject local a anesthetic into a dental patient. The syringe may be operated by human or mechanical operators. The injection fluid may be an anesthetic, medication, lubricant, or any other type of injection fluid suitable for dispensing using a syringe or mechanical means. The buffering agent may be an acid neutralizer, admixture component, catalyst, dye, radioactive marker, or any other type of constituent to be added and mixed with an injection fluid immediately prior to delivery (dispensing) of the combined mixture.

In general, embodiments of the invention include a method and apparatus, referred to as a self-admixing disposable hypodermic needle (also referred to as an "admixing needle" for descriptive convenience), for mixing two constituents into a homogeneous solution upon demand and dispensing from the admixing needle.

A representative embodiment of the admixing needle includes: a delivery needle; a cartridge needle; a male body (reservoir plunger); a female body (reservoir); a delivery needle cap; a cartridge needle cap; and an identification label and sterility seal. The delivery needle includes: a bevel point; a body; a blunt end; and a lumen. The cartridge needle includes: a bevel point; a body; a blunt end; and a lumen. The male body (reservoir plunger) includes: a needle receiver; a first seal ring; a second seal ring; a third seal ring; mixing rings; a tapered nose; an intersecting fluid pathway; an insertion stop surface; and a needle adhesive. The female body (reservoir) includes: a cavity; a cartridge needle receiver; mixing rings; a fluid bypass groove; an end ring snap lock; an external female groove; an external male spline; a female threaded area; a chamfered lead-in; and a needle adhesive. The delivery needle cap includes: an internal spline; a label area; an internal conical area; a chamfer; an external spline and a syringe cap stop ring. The cartridge needle cap includes: an external spline; a label area; an internal conical area; and a chamfer. The identification label and sterility seal includes: markings; a base color; a sterility adhesive; and a colored stripe. The aspirating syringe includes: a male threaded area; a cartridge port; a view port; a thumb ring; a syringe plunger; a harpoon barb; a finger grip; a finger bar; and a needle access lumen. The injection fluid (in this example Lidocaine) cartridge includes: a stopper; a diaphragm; a metal diaphragm clamp; a glass body; and a reservoir area.

In an embodiment, the process of creating a homogeneous mixture of two or more solutions into a final preparation upon demand facilitated by a admixing needle may including the steps of:

a) providing a admixing needle comprising a first receptacle capable of containing at least one or more of the constituents, b) providing a cartridge apparatus (e.g., Lidocaine or the like) being a second receptacle capable of containing at least one or more of the constituents, c) the admixing needle and the cartridge apparatus having the ability to be conjoined, facilitated by a said aspirating syringe assembly apparatus or the like, d) the aspirating syringe assembly apparatus or the like, having the ability to preferentially arrange and maintain the coaxial and linear positions of the admixing needle and the cartridge apparatus during the mixing process and during their kinetic mechanical interactions, e) the aspirating syringe assembly apparatus or the like, having the ability to interact with, and manipulate the longitudinal position of the stopper of the cartridge apparatus during the mixing and delivery process, f) the posterior longitudinal motion of the cartridge stopper has the ability to increase the volume of the injection fluid cartridge reservoir area whereby decreasing the pressure on the solution within the reservoir, g) the anterior longitudinal motion of the stopper has the ability to decrease the volume of the Injection fluid cartridge reservoir area whereby increasing the pressure on the solution within the reservoir area, h) the mechanical interaction, position, and geometry of the male body (reservoir plunger) and the female body (reservoir) to create a constituent fluid reservoir bounded by the male body first ring, which interacts circumferentially with the smooth inside portion of the female body cavity and the posterior end of the female body cavity capable of containing one or more constituent fluids, i) the posterior motion applied to the male body (reservoir plunger) through the interaction of the delivery needle cap internal conical area, to the male body tapered nose, j) the posterior longitudinal motion of the male body (reservoir plunger) within the female body (reservoir) reduces the volume of the female body cavity area, k) the tactile and audible indication of the second seal ring on the male body flexing radially to pass longitudinally under and passed the female body end ring snap lock, l) the posterior and longitudinal ingress motion stop provided by the male body insertion stop surface contacting the anterior surface of the female body, m) the tactile and audible indication of the third seal ring on the male body flexing radially to pass longitudinally under and passed the female body end ring snap lock which irreversibly locks the male body (reservoir plunger) into the female body (reservoir), n) the fluid path created from the Injection fluid cartridge reservoir area to the delivery needle bevel point end after the male body first seal ring passes under the female body fluid bypass groove which completes the bi-directional fluid circuit via the cartridge needle lumen, the female body syringe lumen, the female body and male body mixing rings, the female body fluid bypass groove, around the outside of the male body first seal ring, to the male body second seal ring which prohibits the anterior fluid flow within the female body cavity and redirects the fluid to the male body needle receiver, the delivery needle lumen via the male body intersecting fluid pathway, and out of the delivery needle at the bevel point end, o) the pre-mixing of the at least one constituent contained in the female body cavity of the female body (reservoir) of the admixing needle when it is displaced through the cartridge needle lumen into the Lidocaine or other injection fluid cartridge held within the aspirating syringe by the higher pressure applied to the solution due to a posterior longitudinal force applied to the delivery needle cap and the interaction of the said delivery needle cap internal conical area, to the male body tapered nose and the posterior travel of the male body (reservoir plunger) within the female body (reservoir), p) the pre-mixing of the at least two constituent fluids, powders, or gasses in the Lidocaine or other injection fluid cartridge being the result of the turbulence and vortices created by the at least one fluid being expelled from the posterior cartridge needle lumen at the cartridge needle bevel end at a higher pressure than the at least one fluid contained in the Injection fluid cartridge reservoir area and/or the cartridge stopper moving posteriorly, q) the removal of the delivery needle cap from the conjoined said admixing needle and said aspirating syringe by applying clockwise rotational force to the delivery needle external spline and a simultaneous anterior longitudinal force to displace the delivery needle cap, r) the displacement of the at least two homogeneously mixed fluids from the injection fluid cartridge through the entirety of the admixing needle by applying an anterior linear force to the syringe thumb ring which translates the Lidocaine cartridge stopper anteriorly to increase the pressure within the Injection fluid cartridge reservoir area, s) the turbulence and vortices created by the at least two pre-mixed fluids contained in the injection fluid cartridge reservoir area passing over the male body mixing rings and the female body mixing rings to partially or fully affect the homogeneous admixing of the at least two fluids while being excised, t) the turbulence and vortices created by the at least two pre-mixed fluids contained in the injection fluid cartridge reservoir area passing over the male body first seal ring and under the female body fluid bypass groove to partially or fully affect the homogeneous admixing of the at least two fluids while being excised, u) the turbulence and vortices created by the at least two pre-mixed fluids contained in the injection fluid cartridge reservoir area passing through the male body intersecting fluid pathway to partially or fully affect the homogeneous admixing of the at least two fluids while being excised, v) the turbulence and vortices created by the at least two pre-mixed fluids contained in the injection fluid cartridge reservoir area passing through the male body needle receiver and through the delivery needle lumen to partially or fully affect the homogeneous mixing of the at least two fluids prior to being excised, w) the placement of the delivery needle bevel point end parenterally into the squamous stratified epithelium or the like and applying posterior linear force to the syringe thumb ring to create a negative pressure within the injection fluid cartridge reservoir area, x) the negative pressure thereby being transmitted through the pre-established, bi-directional fluid communion pathway to the delivery needle bevel point end through airtight sealing of the admixing needle components and the interaction of the cartridge needle body exterior surface with the cartridge diaphragm, y) the negative pressure created within the fluid flow system to verify that the delivery needle bevel point end is not within the venous or arterial system of the patient by looking for blood within the Injection fluid cartridge glass body and reservoir areas through the syringe cartridge port or the aspirating syringe viewport, At least two solutions may be homogeneously mixed to create one preparation just prior to hypodermically delivering them parenterally into the squamous stratified epithelium or the like near nerves that it is desirous to stop the signaling cascade of pain impulses to the brain to facilitate one or more dental or medical procedures which would normally cause an excess of noxious pain signals to the patient preventing the procedure or procedures.

A feature of the illustrative embodiments includes the ability to remove the Injection fluid cartridge after it is empty from the aspirating syringe while the admixing needle is still conjoined to the aspirating syringe to reload additional fully charged injection fluid cartridges for unmixed (unbuffered) use after the patient's nerve signaling pathway has been substantially inhibited from previous buffered or unbuffered local anesthetic injections.

Another illustrative feature includes the mechanical position of the identification label and security seal spanning circumferentially and at least 360 degrees over the delivery needle cap label area and the cartridge needle cap label area to maintain the sterility of the internal areas including the fluid reservoir, delivery needle, and cartridge needle of the admixing needle.

Another illustrative feature includes the human-readable text, machine-readable bar code or two dimensional universal identification (2D UID) markings, and/or external color or laterally displaced color stripe on the outside of a said identification label and security seal to identify desirous features of the admixing needle not visible from the outside including but not limited to delivery needle length and or gage.

Another illustrative feature includes the identification label sterility adhesive located on the opposite side of the identification label and security seal to the markings which secures it to the admixing needle delivery needle and cartridge needle caps.

Another illustrative feature includes the removal of only the cartridge needle cap from the admixing needle by applying rotational and posterior linear forces to the cartridge needle cap to disengage the sterility seal and identification label adhesive whereby permitting removal of the cartridge needle cap from the delivery needle cap.

Another illustrative feature includes the insertion of the cartridge needle bevel end into the aspirating syringe needle access lumen to align it coaxially with the cartridge diaphragm.

Another illustrative feature includes further travel of the cartridge needle bevel end into the aspirating cartridge needle access lumen whereby piercing the cartridge diaphragm with the admixing needle cartridge needle bevel end.

Another illustrative feature includes the mechanical position and interaction of the diaphragm seal on the injection fluid cartridge being made of an elastomericly compounded material and having the ability to allow the ingress of the cartridge needle bevel end via puncture during the mechanical interconnection of the admixing needle with the aspirating syringe.

Another illustrative feature includes the interaction of the cartridge needle of the admixing needle to the injection fluid cartridge to create a bidirectional fluid communication path which facilitates the at least one first solution contained within the admixing needle to transfer to the reservoir area of the injection fluid cartridge.

Another illustrative feature includes the interaction of the cartridge needle on the admixing needle to the injection fluid cartridge reservoir area create a fluid communication path which facilitates the transfer of the at least one second solution contained within the reservoir area of the injection fluid cartridge apparatus to the admixing needle.

Another illustrative feature includes the mechanical position and interaction of the diaphragm seal on the injection fluid cartridge being made of an elastomericly compounded material and having the ability to provide and maintain a pressure seal around the body of the cartridge needle during the mechanical interconnection of the admixing needle with the aspirating syringe assembly apparatus and during the entire mixing and admixed fluid delivery process.

Another illustrative feature includes an attachment method capable of conjoining the female body female threaded area on said admixing needle to the syringe male threaded area on the said aspirating syringe assembly apparatus like but not limited to a set of matched male and female screw threads.

Another illustrative feature includes the placement of the female body chamfered lead-in located on the female body of the admixing needle over the male threads on the aspirating syringe assembly apparatus until the female body female threads contact the male threads on the aspirating syringe assembly apparatus.

Another illustrative feature includes the interaction of the at least one longitudinally said delivery needle cap internal spline member with the at least one receiving said mentioned female body external female spline or groove member which allows longitudinal posterior motion while transferring the radial motion applied to the delivery needle cap to conjoin the admixing needle fully to the aspirating syringe assembly apparatus.

Another illustrative feature includes the placement of the injection fluid cartridge within an aspirating syringe apparatus with the ability to be conjoined to the admixing needle to allow mechanical interaction and bidirectional fluid flow between their fluid containing components.

Another illustrative feature includes the interaction of the harpoon barb which is attached to the syringe plunger, which is attached to the thumb ring all being components of the aspirating syringe wherein the harpoon barb anterior point pierces the posterior end of the cartridge stopper, being made of an elastomeric material, rubber or the like, due to a sharp force being anteriorly applied to the posterior end of the thumb ring whereby preventing the barb from being easily removed from the stopper during the posterior motion of the thumb ring and transferring the posterior linear force from the thumb bring to the stopper.

Another illustrative feature includes the injection fluid (e.g., Lidocaine) cartridge stopper, while being circumferentially engaged to the smooth inside circular surface of the injection fluid cartridge glass body which bounds the cartridge reservoir area's volume in conjunction with the cartridge diaphragm, is able to travel longitudinally given an appropriate amount of anterior or posterior mechanical force transmitted through the harpoon barb, syringe plunger, and thumb ring being components of the aspirating syringe assembly apparatus provides linear motion of the cartridge stopper within the cartridge.

Another illustrative feature includes the conjoining of the harpoon barb to the cartridge stopper thereby transferring any posterior motion from the thumb ring to the cartridge stopper and reduce the pressure applied to the at least two fluids contained within the cartridge glass body by increasing the volumetric area containing the at least two fluids to create a vacuum.

Another illustrative feature includes the conjoining of the harpoon barb to the cartridge stopper thereby transferring any anterior motion from the thumb ring to the cartridge stopper and induce additional pressure to the at least two fluids contained within the cartridge reservoir area by reducing the volumetric area containing the at least two fluids.

Another illustrative feature includes the ability to replace the delivery needle cap over the admixing needle after completing one or more injections to protect the dentist or medical practitioner from accidental needle sticks.

Another illustrative feature includes the ability to replace the delivery needle cap over the admixing needle after completing one or more injections and to facilitate removal from the aspirating syringe for safe disposal. And another illustrative feature includes the ability to replace the cartridge needle cap over the admixing needle after completing one or more injections for safe disposal.

In view of the foregoing, it will be appreciated that present invention provides significant improvements in syringes by providing a self-admixing disposable hypodermic needle. The foregoing relates only to the exemplary embodiments of the present invention, and that numerous changes may be made therein without departing from the spirit and scope of the invention as defined by the following claims.

TABLE OF COMPONENTS AND ELEMENT NUMBERS

| Component | Number |
|---|---|
| delivery needle | 100 |
| delivery needle bevel point | 101 |
| delivery needle body | 102 |
| delivery needle blunt end | 103 |
| delivery needle lumen | 104 |
| cartridge needle | 200 |
| cartridge needle bevel point | 201 |
| cartridge needle body | 202 |
| cartridge needle blunt end | 203 |
| cartridge needle lumen | 204 |
| male body (reservoir plunger) | 300 |
| male body needle receiver | 301 |
| male body first seal ring | 302 |
| male body second seal ring | 303 |
| male body third seal ring | 304 |
| male body mixing rings | 305 |
| male body tapered nose | 306 |
| male body intersecting fluid pathway | 307 |
| male body insertion stop surface | 308 |
| male body needle adhesive | 309 |
| female body (reservoir) | 400 |
| female body cavity | 401 |
| female body needle receiver | 402 |
| female body mixing rings | 403 |
| female body fluid bypass groove | 404 |
| female body end ring snap lock | 405 |
| female body external female groove | 406 |
| female body external male spline | 407 |
| female body female threaded area | 408 |
| female body chamfered lead-in | 409 |
| female body needle adhesive | 410 |
| delivery needle cap | 500 |
| delivery needle cap internal spline | 501 |
| delivery needle cap label area | 502 |
| delivery needle cap internal conical area | 503 |
| delivery needle cap chamfer | 504 |
| delivery needle cap external spline | 505 |
| delivery needle cap syringe cap stop ring | 506 |
| cartridge needle cap | 600 |
| cartridge needle cap external spline | 601 |
| cartridge needle cap label area | 602 |
| cartridge needle cap internal conical area | 603 |
| cartridge needle cap chamfer | 604 |
| identification label and sterility seal | 700 |
| identification label markings | 701 |
| Identification label base color | 702 |
| identification label sterility adhesive | 703 |
| identification label colored stripe | 704 |
| syringe (e.g., aspirating syringe) | 800 |
| syringe male threaded area | 801 |
| syringe cartridge port | 802 |
| syringe view port | 803 |
| syringe thumb ring | 804 |
| syringe plunger | 805 |
| syringe harpoon barb | 806 |
| syringe finger grip | 807 |
| syringe finger bar | 808 |
| needle access lumen | 809 |
| injection fluid (e.g., Lidocaine ®) cartridge | 900 |
| cartridge stopper | 901 |
| cartridge diaphragm | 902 |
| cartridge metal diaphragm clamp | 903 |
| cartridge glass body | 904 |
| cartridge reservoir area | 905 |
| self-admixing disposable hypodermic needle | 1000 |

The invention claimed is:

1. An admixing needle for use with a syringe holding a cartridge containing an injection fluid, comprising:

a delivery needle comprising a delivery needle bevel point axially aligned with and in communication with a delivery needle lumen;

a cartridge needle comprising a cartridge needle bevel point axially aligned with and in communication with a cartridge needle lumen;

a reservoir containing an additive connected in fluid communication between the delivery needle and the cartridge needle with the delivery needle lumen and the cartridge needle lumen coaxially aligned and connected to opposing ends of the reservoir;

a delivery needle cap removably placed in a protective position over the delivery needle, coaxially aligned with the delivery needle, and removably connected to the reservoir;

a cartridge needle cap removably placed in a protective position over the cartridge needle, coaxially aligned with the cartridge needle, and removably connected to the reservoir;

a reservoir plunger coaxially aligned with the delivery needle and the cartridge needle, and positioned to translate within the reservoir for forcing the additive out the reservoir;

the admixing needle configured for removable attachment to an end of the syringe with the reservoir axially aligned with the cartridge and the cartridge needle bevel point inserted into the cartridge and in fluid communication with the injection fluid within the cartridge and the delivery needle cap positioned to push the reservoir plunger axially toward the syringe to force the additive out the reservoir, through the cartridge needle lumen, through the cartridge needle bevel point, and into the cartridge to create an injection mixture within the cartridge comprising the injection fluid and the additive;

the admixing needle further configured for communicating, under pressure created by operation of the syringe, the injection mixture from the cartridge, through the cartridge needle bevel point, through the cartridge needle lumen, through the reservoir, through the delivery needle lumen, and through the delivery needle bevel point.

2. The admixing needle of claim 1, further comprising:
a mixing surface of the reservoir;
a mixing surface of the reservoir plunger;
the admixing needle further configured for communicating, under pressure created by operation of the syringe, the injection mixture from the cartridge past the mixing surface of the reservoir and the mixing surface of the reservoir plunger to further mix the injection mixture.

3. The admixing needle of claim 1, wherein the injection fluid is acidic and the additive is an acid neutralizer.

4. The admixing needle of claim 1, wherein the injection fluid comprises Lidocaine and the additive comprises sodium bicarbonate.

5. The admixing needle of claim 1, wherein the syringe is an aspirating syringe.

6. The admixing needle of claim 1, further comprising:
a frangible label and sterility seal adhered to the delivery needle cap and to the delivery needle cap;
wherein the cartridge needle cap is configured to rotate with respect to the delivery needle cap to break the label and sterility seal.

7. The admixing needle of claim 1, wherein:
the reservoir plunger is configured to latch to the reservoir;
latching of the reservoir plunger to the reservoir is configured to emit an audible and tactile click when the reservoir plunger is fully inserted into the reservoir.

8. The admixing needle of claim 1, wherein:
the reservoir further comprises a fluid bypass groove;
the reservoir plunger further comprises a seal ring configured to open a fluid communication path between the delivery needle and the cartridge needle through the fluid bypass groove when the reservoir plunger is forced past the fluid bypass groove.

9. The admixing needle of claim 1, wherein:
the reservoir further comprises a latch to capture the reservoir plunger in the reservoir when the reservoir plunger has been fully inserted into the reservoir;
the reservoir further comprises a fluid bypass groove;
the reservoir plunger further comprises a seal ring configured to open a fluid communication path between the delivery needle and the cartridge needle through the fluid bypass groove when the reservoir plunger is forced past the fluid bypass groove and into engagement with the latch.

\* \* \* \* \*